United States Patent [19]

Ellinghaus

[11] Patent Number: 5,693,221

[45] Date of Patent: Dec. 2, 1997

[54] CYCLONIC LIQUID-SEPARATING UNIT

[75] Inventor: Wolfgang Ellinghaus, Gerlingen, Germany

[73] Assignee: Dürr Dental GmbH & Co. KG, Bietigheim-Bissingen, Germany

[21] Appl. No.: 495,401

[22] PCT Filed: Nov. 5, 1994

[86] PCT No.: PCT/EP94/03635

§ 371 Date: Oct. 25, 1995

§ 102(e) Date: Oct. 25, 1995

[87] PCT Pub. No.: WO95/14440

PCT Pub. Date: Jun. 1, 1995

[30] Foreign Application Priority Data

Nov. 25, 1993 [DE] Germany ............... 43 40 193.7

[51] Int. Cl.⁶ ..................... B01D 19/00; B01D 21/26
[52] U.S. Cl. ............. 210/188; 210/512.1; 210/512.3; 55/459.1; 96/195; 209/715; 415/169.2; 433/92
[58] Field of Search ............... 433/92; 210/512.3, 210/512.1, 188; 55/459.1; 209/715; 96/195; 415/169.2

[56] References Cited

U.S. PATENT DOCUMENTS 4,842,478  6/1989  Durr et al. ................. 433/92
4,919,826  4/1990  Alzner ...................... 210/788
5,330,641  7/1994  Cattani ..................... 210/188

FOREIGN PATENT DOCUMENTS 0 237 708  9/1987  European Pat. Off. .
0 524 455  1/1993  European Pat. Off. .
39 16 742  12/1990  Germany .

OTHER PUBLICATIONS

PTO 96–5544 Translation of German Patent No. 3,916,742 A1, Dec. 6, 1990.

PTO 96–5543 Translation of European Patent No. 0 524 455 A1, Jan. 27, 1993.

*Primary Examiner*—David A. Reifsnyder
*Attorney, Agent, or Firm*—Lowe, Price, LeBlanc & Becker

[57] ABSTRACT

A liquid-separating unit for dental purposes has, flange-mounted on a suction machine, a liquid-separating cyclone comprising a housing which surrounds a cyclone chamber (22) and into which a motor shaft (26) of the suction machine is passed. The latter carries at the end a pump impeller (42) for discharging liquid separated in the cyclone, and also a rotationally symmetrical air discharge part (28) the peripheral wall of which tapers at least in a portion (36) in the direction from the pump impeller (42) towards an outlet pipe (96) for cleaned air.

19 Claims, 3 Drawing Sheets

CYCLONIC LIQUID-SEPARATING UNIT

FIELD OF THE INVENTION

The invention relates to a liquid-separating unit according to the precharacterising clause of claim 1.

BACKGROUND OF THE RELATED ART

A separating unit of that kind is described in EP 0 237 708 B1, which is coaxially mounted on a suction machine. It comprises a liquid-separating cyclone through which the motor shaft of the suction machine is passed. The end of the motor shaft carries a pump impeller which carries liquid deposited in the cyclone out of the cyclone, which is under a vacuum, and into the public drains. To prevent a direct flow connection between the inlet of the cyclone and its outlet which is connected to the suction machine, a substantially cylindrical air discharge part, for directing air into an outlet pipe, is provided in the interior of the cyclone.

If such a separating unit is subjected to very large quantities of surge water, droplets of liquid that stray into the interior of the air discharge part may still pass from there into the interior of the suction machine.

By means of the present invention, therefore, a separating unit according to the precharacterising clause of claim 1 is to be developed in such a manner that any liquid possibly entering the air discharge part is moved towards the pump impellar.

This problem is solved according to the invention by a suction unit having the features specified in claim 1.

A liquid-separating cyclone having an air discharge part connected to a rotating drive shaft is already known in principle from DE 39 16 742 A1. That air discharge part, however, has a substantially cylindrical geometry and is not entirely satisfactory with regard to returning liquid fractions still found there.

SUMMARY OF THE DISCLOSURE

In the case of the liquid-separating cyclone constructed in accordance with the invention, by constricting the revolving air discharge part any liquid fractions still deposited there are forcibly returned to the pump impeller, where the air discharge part has its largest diameter.

Advantageous developments of the invention are specified in subclaims.

A cross-sectional geometry of the air discharge part of the kind specified in claim 2 is advantageous with a view to a favourable flow behaviour for the air and, at the same time, with a view to a reliable return of deposited liquid fractions.

As a result of the development according to claim 3, the air discharged by the cyclone is subjected in the lead-out part to an additional centrifugal effect, which is advantageous with a view to separating residual fractions of liquid.

In the case of a separating unit according to claim 4, it is ensured that liquid fractions of the separated mixture, which liquid fractions have been returned in the air discharge part to the pump impeller are taken by the pump impeller directly at the end of the air discharge part and are finally fed effectively into the liquid outlet pipe.

As a result of the development or the invention according to claim 5, the quantity of air leaving the liquid-separating cyclone is forcibly given additional momentum, which is advantageous with a view to an effective separation of the liquid even before the air enters the air discharge part. This improvement in the liquid separation is obtained without significant additional cost, since the pump impeller has to be equipped with pump vanes in any case.

As a result of the development of the invention according to claim 6, the air discharged from the liquid-separating cyclone is diverted into the air discharge part in a substantially smooth flow.

In the case of a separating unit according to claim 7, there is a very effective dynamic seal between the liquid outlet channel and the liquid-separating cyclone.

Under strong surge conditions, splashes may form in the annular space between the cyclone wall and the air discharge part. In the case of a separating unit according to claim 8, it is ensured that those splashes are retained in the interior of the cyclone.

In that connection, with the development of the invention according to claim 9, the baffle flange is altogether divided in two. There is thus a sealing surface between two thin components moved relative to each other, which components can be made to fit with a small clearance more easily than can the mechanically stable and thick cyclone wall.

If the stationary part of the baffle flange is constructed in accordance with claim 9, any liquid that has passed over the baffle flange is able to flow along the same and downward under the effect of gravity and drip off at the lower end of the stationary part of the baffle flange.

The development of the invention according to claim 11 also serves to achieve reliable sealing of the upper end of the revolving air discharge part with respect to the cyclone housing.

The dynamic sealing of the upper end of the air discharge part according to claim 12 and according to claim 13 provides for a once more improved sealing of the upper end of the air discharge part.

With the development of the invention according to claim 14, the air discharged from the liquid-separating cyclone is taken substantially smoothly and without turbulence by a conically widening suction opening of the suction machine.

In this connection, in accordance with claim 15, a dynamic seal is obtained here also by means of the axial ribs provided on the outside of the outlet pipe.

The development of the invention according to claim 16 is advantageous with a view to preventing any solids particles that may be present in the separated liquid from becoming wedged between the underside of the pump impeller and the opposing boundary surface of the pump chamber.

If a liquid-separating unit is built directly onto a solution machine in accordance with claim 17, a compact separating unit having a mechanically simple construction and only a single drive motor is obtained.

DETAILED DESCRIPTION OF THE PREFERRED EMBODIMENTS

Figure 1:
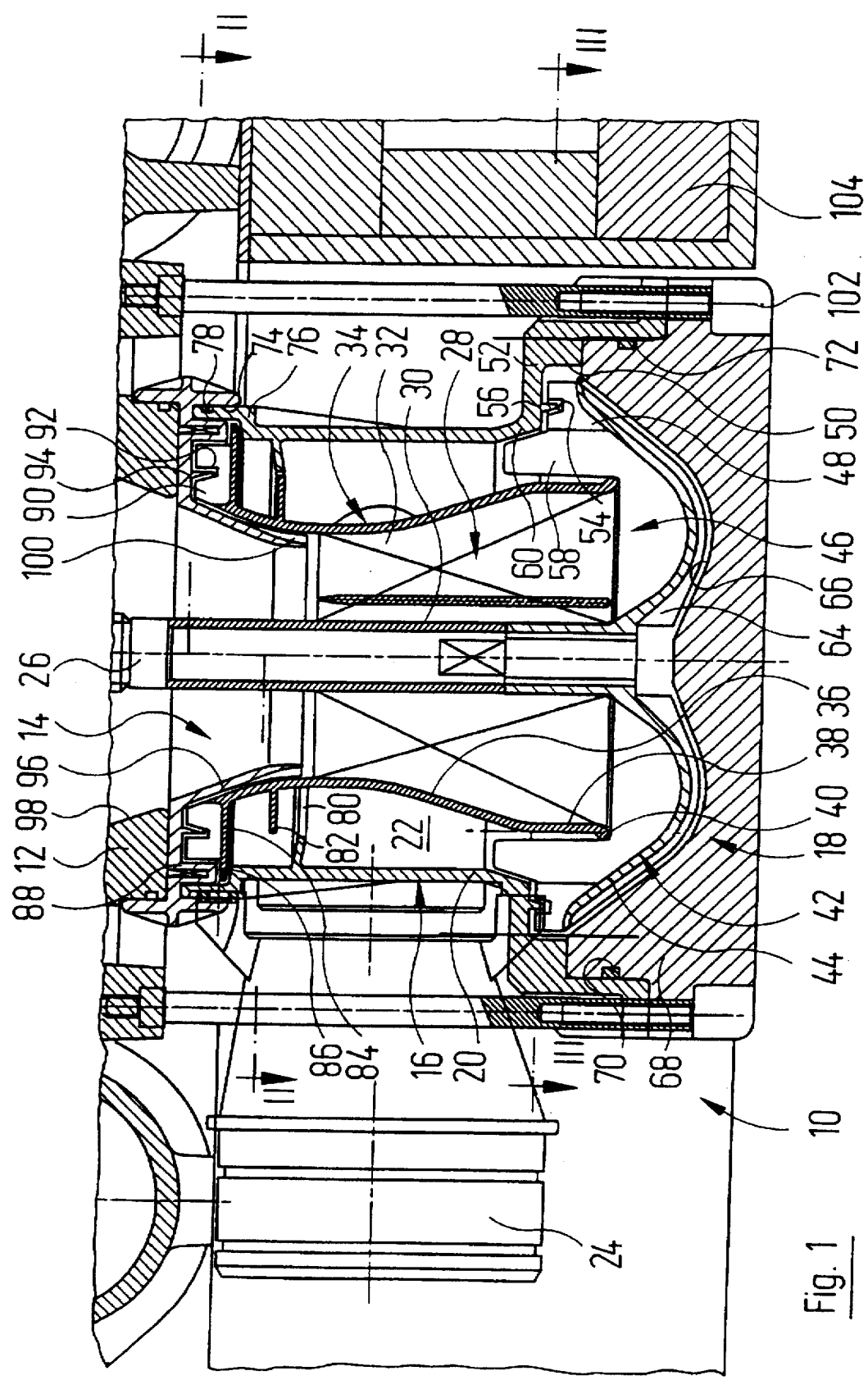
FIG. 1 shows an axial section through a liquid-separating cyclone together with the end of a suction machine on which said cyclone is flange-mounted.
Figure 2:
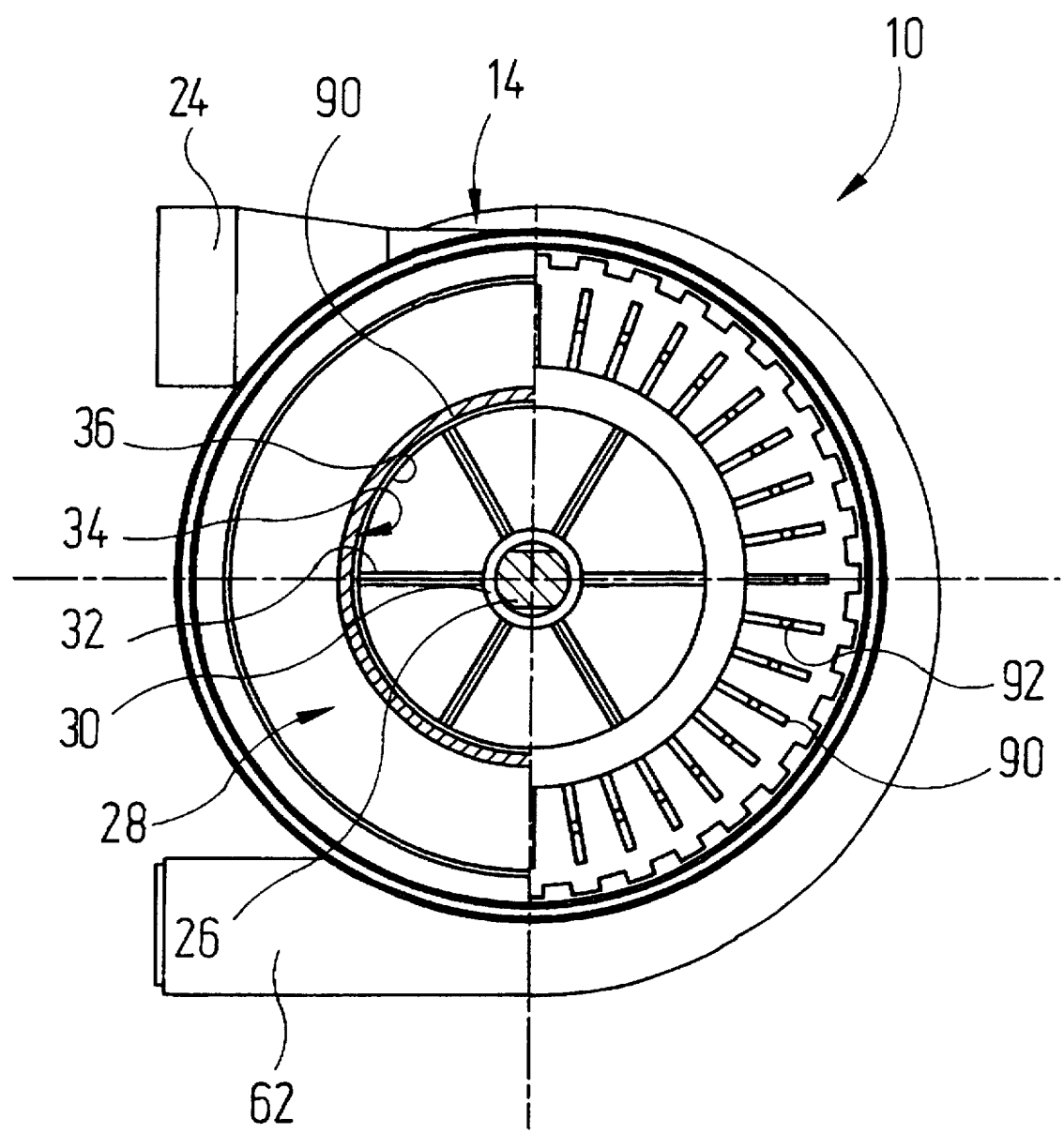
FIG. 2 shows a modified section through an upper end portion of the liquid-separating cyclone along the line of section II—II in FIG. 1.

In FIG. 1, reference numeral 10 denotes a liquid-separating cyclone in its entirety, which is fastened as a block to the lower end of a housing 12 of a suction machine.

The separating cyclone 10 has a lid-like upper housing part 14, a substantially rotationally symmetrical middle housing part 16 and a lower housing part 18.

The middle housing part 16 has a cylindrical peripheral wall 20 which defines a cyclone chamber 22 into which an inlet pipe 24 opens tangentially. When the machine is ready for use, the inlet pipe 24 is connected to a line which is connected to the depository of one or more dental work stations and receives from there a mixture of air and liquid fractions obtained in a patient's mouth during working; the liquid fractions may comprise, in addition to saliva and water, also drillings (removed bone material and filling material).

Extending through the housing parts 14 to 18 is the lower end of a motor shaft 26 of the suction machine, which motor shaft carries in the part thereof to be imagined above FIG. 1, in addition, the fan wheel of the suction machine and the rotor of an electric drive motor.

Seated on the motor shaft 26 is an air discharge part designated 28 in its entirety which has a hub portion 30, a plurality of radial vanes 32 distributed in the circumferential direction and a rotationally symmetrical guide wall 34. The guide wall 34 which thus rotates together with the motor shaft 26 defines the inner boundary of the cyclone chamber 22. As can be seen from the drawing, the guide wall 34 is curved convexly viewed from the inside of the air discharge part 28. More accurately, viewed in axial section, there is an upper, substantially circular-arcuate guide wall portion 36 adjoined at the bottom by a guide wall portion 38 that is shorter in comparison and substantially cylindrical and that carries at its free end a guide wall portion 40 extending outward and downward in the form of a conical crown.

The guide wall portion 38 engages in a pimp impeller, designated 42 in its entirety, which is seated on the free lower end of the motor shaft The pump impeller 42 has a lower end plate 44 which defines a substantially V-shaped circumferential channel that is open towards the top, the vertex of the v being replaced by a generously sized, substantially circular-arcuate base portion.

The upper side of the pump impeller 42 carries a plurality of pump vanes 46 distributed in the circumferential direction, between which pump vanes 46 yet more extraction vanes 48 are situated at the edge. The radially outermost end portions of the pump vanes 45 have the same geometry as that of the extraction vanes 48. The extraction vanes 48 extend into a spiral liquid outlet channel 50 constructed in a foot portion 52 of the middle housing part 16, which foot portion 52 is drawn radially outward.

Provided in the upper side of the extraction vanes 48 and the corresponding end portions of the pump vanes 46 are notches 54 which run with a small amount of clearance over a rib 56 hanging down from the top wall of the outlet channel 50. In this manner, the outlet channel 50 is dynamically sealed with respect to the cyclone chamber 22.

As can be seen from FIG. 1, the pump vanes 46 have a 90° offset so that the lower end of the air discharge part 28 can engage into the pump impeller 42. An upper end portion 58 of the pump vanes 46 is drawn up above the top wall of the outlet channel 50 and projects into a cylindrically widening lower end portion 60 of the peripheral wall 20 of the cyclone chamber, a sloping outer edge of the end portions 58 running with a small amount of clearance from the inner surface of the end portion 60 of the peripheral wall 20.

Figure 3:
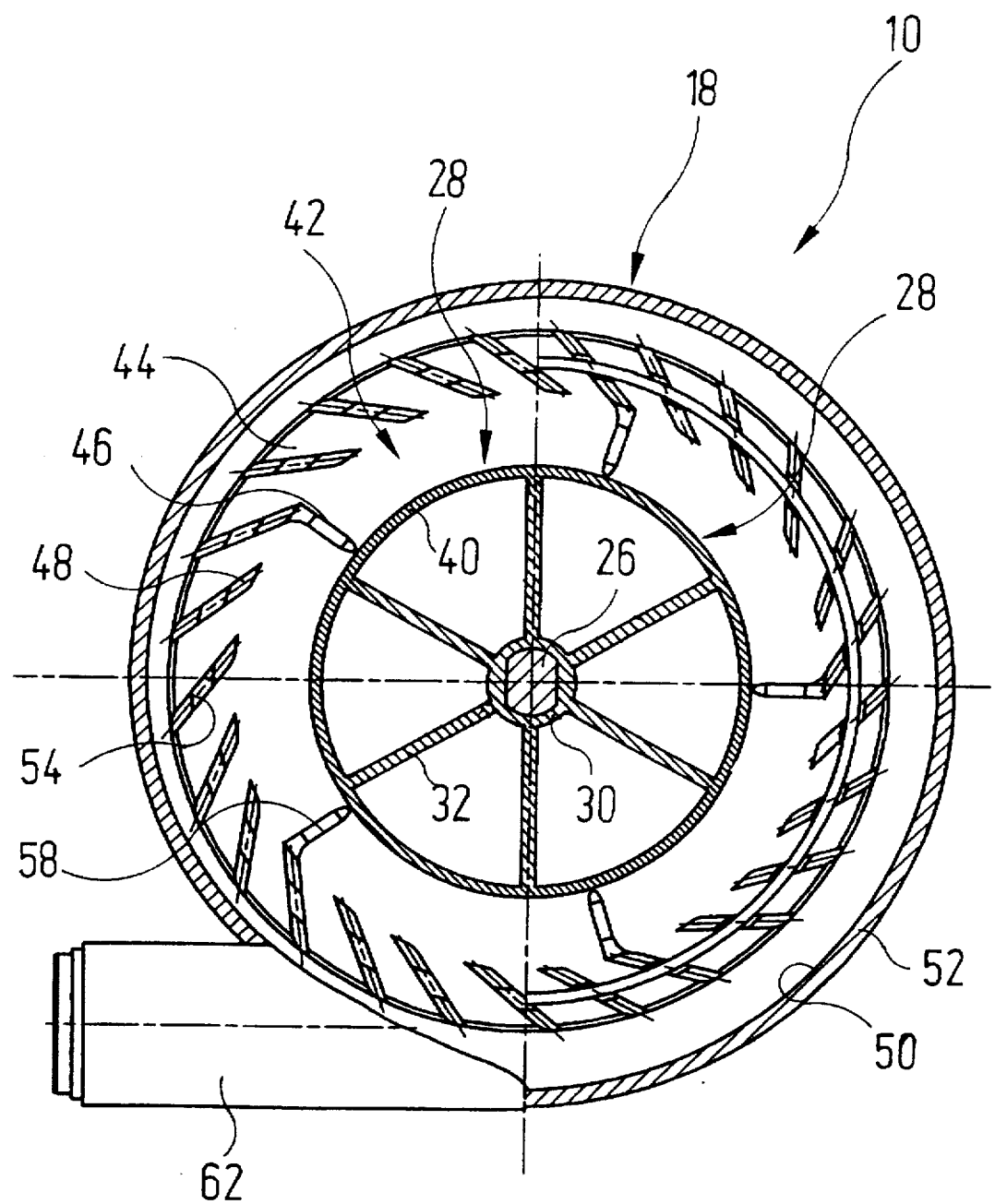
FIG. 3 shows a section through the lower end portion of the liquid-separating cyclone along the line of section III—III in FIG. 1.

As can be seen from FIG. 3, a liquid outlet pipe 62 is connected to the outlet channel 50.

As FIG. 1 shows, there are provided on the underside of the end plate 44 of the pump impeller 42 circumferentially distributed pump ribs 64 which maintain a radially outward flow of the liquid on the underside of the pump impeller 42 and thus prevent solids particles from entering the gap between the underside of the pump impellar 42 and the correspondingly shaped upper side 66 of the lower housing part 18.

As can also be seen from FIG. 1, the lower housing part 18 has a cylindrical extension 68 with which it engages in a form-fitting manner in a corresponding cylindrical opening 70 at the lower end of the middle housing part 16, an O-ring seal 72 additionally being provided.

The upper housing part 14 has in its underside a cylindrical recess 74 in which an upper cylindrical end portion 76 of the middle housing part 16, sealed by O-ring seals 78, is seated.

In the upper portion the peripheral wall 20 carries a helical, stationary baffle flange 80 which projects radially inward and slopes in the radially inward direction. At a small radial distance from the latter, the air discharge part 28 carries a revolving baffle flange 82 which is axially flush with the highest portion of the helical baffle flange 80.

Above the baffle flange 82, the air discharge 28 carries, in the immediate vicinity of its end, a revolving sealing flange 84 which engages with a small amount of clearance in a groove 86 defined between a shoulder formed in the end portion 76 of the housing part 16 and a sealing rib 88 which extends all the way round on the upper housing part 14.

On the upper side of the sealing flange 84, pump vanes 90 lying radially inside the sealing rib 88 are provided, the upper edges of which are again each provided with a notch 92. The notches 92 run with a small amount of clearance over a sealing rib 94 which is carried by and hangs down from the end wall of the lid-like housing part 18.

The above-described structural elements 84 to 94 provide for a dynamic sealing of the upper end of the air discharge part 28 with respect to the middle housing part 16 and, therewith, with respect to the cyclone chamber 22. The baffle flanges 80 and 82 form a spray water baffle arranged upstream of that dynamic seal.

As FIG. 1 shows, the upper housing part 14 has a downward-hanging outlet pipe 96 for air that has been freed of liquid. The inclination of the outlet pipe 96 is selected in view of the inclination of the wall surface of an inlet opening 98 which is formed in the lower portion of the housing 12 of the suction machine. The upper end portion of the air discharge part 28 substantially follows the geometry so defined of the outer surface of the outlet pipe 96 except, however, that towards the free end of the outlet pipe 96 there Is a widening but narrow wedge-shaped gap between the outer surface of the outlet pipe 96 and the inner surface of the air discharge part 28. In that gap, there are provided on the outside of the outlet pipe 96 axial ribs 100 the outer edges of which follow the inner surface of the air discharge part 28 with a small amount of clearance.

The housing parts 14, 16, 18, the air discharge part 28 and the pump impeller 42 are all injection-moulded parts made from glass-fibre-reinforced plastics material, and the various housing parts are fastened to the housing 12 of the suction machines by bolts 102.

In FIG. 1, there is additionally shown a sound absorber 104 which surrounds the liquid-separating cyclone 10.

The purpose of the above description and examples is to illustrate preferred embodiments of the present invention without implying any limitation. It will be apparent to those of skill in the art that various modifications and variations may be made to the device and method of the present invention without departing from the spirit or scope of the invention and such modifications and variations are considered comprehended within the disclosed invention.

I claim:

1. A liquid-separating unit for use with dental-care equipment, comprising:

a housing which defines a cyclone chamber and a pump chamber arranged beneath the cyclone chamber; and a pump impeller which has pump vanes and is carried by a drive shaft extending through the cyclone chamber, the housing comprising an inlet pipe and a first outlet pipe for air and a second outlet pipe for liquid, there being arranged in the cyclone chamber an air discharge for directing air into the first outlet pipe which surrounds the drive shaft coaxially and is arranged between the inlet pipe and the first outlet pipe the air discharge part is seated on the drive shaft for common rotation therewith and having a diminishing cross-section at least in a portion thereof from the pump impeller towards the first outlet pipe, the point of smallest cross-section lying adjacent the first outlet pipe.

2. The separating unit according to claim 1, a tapering portion of the air discharge part has a substantially circular-arcuate geometry viewed in axial section.

3. The separating unit according to claim 1, wherein:

the air discharge part is joined by radial vanes to a hub portion which is seated on the drive shaft.

4. The separating unit according to claim 1, wherein:

a lower end of the air discharge part engages in an axial direction into an upper side of pump vanes which are provided on an upper side of the pump impeller.

5. The separating unit according to claim 4, wherein:

the pump vanes have end portions drawn upward in an axial direction and which extend into a lowermost portion of the cyclone chamber.

6. The separating unit according to claim 1, wherein:

a lower end plate of the pump impeller forms a continuously curved reversing channel which is open towards a top thereof.

7. The separating unit according to claim 1, wherein:

radially outward end portions of pump vanes of the pump impeller each have a notch in their upper edge, which notches run with a selected amount of clearance over a rib hanging down from a top wall of the pump chamber.

8. The separating unit according to claim 7, wherein:

additional discharge vanes are provided to the pump impeller, each having a notch in an upper edge, which notches run with a predetermined clearance over a rib depending downward from a top wall of the pump chamber.

9. The separating unit in accordance with claim 7, wherein:

the baffle flange slopes in a radially inward direction.

10. The separating unit according to claim 1, wherein:

an outside of the air discharge part carries a baffle flange which lies above the inlet pipe of the housing.

11. The separating unit according to claim 10, wherein:

an edge of the baffle flange which revolves with the air discharge part runs with a selected radial clearance inside a baffle flange fixed to the housing.

12. The separating unit according to claim 11, wherein:

the baffle flange that is fixed to the housing is helical.

13. The separating unit according to claim 1, wherein:

there is provided at an upper end of the air discharge part a transverse sealing flange which engages into a groove in the housing with a first selected clearance.

14. The separating unit according to claim 13, wherein:

an upper side of the sealing flange carries a plurality of pump vanes distributed in a circumferential direction.

15. The separating unit according to claim 14, wherein:

upper edges of the pump vanes of the sealing flange have notches which run with a second selected clearance under an annular sealing rib carried by a top wall of the housing.

16. The separating unit according to claim 1, wherein:

the first outlet pipe is drawn axially downward from a top wall of the housing, substantially following a shape of an inner surface of an inlet opening of a suction machine, and the upper end of the air discharge part follows an outer contour of the outlet pipe with a first selected clearance.

17. The separating unit according to claim 16, wherein an outside of an end portion of the outlet pipe defines together with an inner surface of the air discharge part a pointed gap which is wedge-shaped in cross-section, and an outside of the outlet pipe carries in that gap a plurality of axial ribs distributed in a circumferential direction, outer edges of the ribs being opposite an inner surface of the air discharge lead-out part with a second selected clearance.

18. The separating unit according to claim 1, wherein:

an underside of the pump impeller is provided with pump ribs extending radially.

19. The separating unit according to claim 1, wherein:

the drive shaft is a motor shaft of a suction machine attached as a block and the drive shaft simultaneously carries a fan wheel of the suction machine.

* * * * *